United States Patent [19]
Larsen et al.

[11] Patent Number: 5,994,577
[45] Date of Patent: *Nov. 30, 1999

[54] AMINOGUANIDINE CARBOXYLATES FOR THE TREATMENT OF NON-INSULIN-DEPENDENT DIABETES MELLITUS

[76] Inventors: Scott D. Larsen, 56 Naples Ct.; Valerie A. Vaillancourt, 4760 Wimbleton Way, both of Kalamazoo, Mich. 49009; Paul D. May, 7890 N. 32nd St., Richland, Mich. 49083; Steven P. Tanis, 7601 Farmington Ave., Kalamazoo, Mich. 49002; John A. Tucker, 3721 Greenleaf Cir., Apt. 301, Kalamazoo, Mich. 49008; Martin D. Meglasson, 5337 Whippoorwill Dr., Kalamazoo; Heinrich J. Schostarez, 6417 Surrey, Portage, both of Mich. 49002

[ * ] Notice: This patent issued on a continued prosecution application filed under 37 CFR 1.53(d), and is subject to the twenty year patent term provisions of 35 U.S.C. 154(a)(2).

[21] Appl. No.: 08/484,547

[22] Filed: Jun. 7, 1995

Related U.S. Application Data

[63] Continuation-in-part of application No. 08/344,274, Nov. 23, 1994, abandoned.

[51] Int. Cl.$^6$ ................................................ C07C 229/00
[52] U.S. Cl. ...................... 560/168; 560/34; 560/145; 562/439; 562/560
[58] Field of Search ........................... 560/34, 168, 145; 562/439, 560

[56] References Cited

U.S. PATENT DOCUMENTS

| | | | |
|---|---|---|---|
| 3,943,253 | 3/1976 | Barer | 424/319 |
| 5,130,324 | 7/1992 | Ulrich | 514/357 |

FOREIGN PATENT DOCUMENTS

| | | |
|---|---|---|
| 0 222 313 A2 | 5/1987 | European Pat. Off. . |

OTHER PUBLICATIONS

M. Pankaskie and M.M. Abdel–Monem, J. Pharm. Sci., 69(9):1000–1004, 1980.

*Primary Examiner*—Michael L. Shippen
*Attorney, Agent, or Firm*—Birch, Stewart, Kolasch & Birch, LLP

[57] ABSTRACT

The present invention provides novel compounds of the formula I and II for the treatment of non-insulin dependent diabetes mellitius (NIDDM) and a new use of known compounds for this purpose.

3 Claims, No Drawings

AMINOGUANIDINE CARBOXYLATES FOR THE TREATMENT OF NON-INSULIN-DEPENDENT DIABETES MELLITUS

CROSS REFERENCE TO RELATED APPLICATIONS

The present application is a continuation-in-part application of U.S. Ser. No. 08/344,274, filed Nov. 23, 1994, now abandoned.

The present invention provides novel compounds and a novel method for treating: non-insulin dependent diabetes mellitus (NIDDM); diabetic complications resulting from excessive non-enzymatic glycosylation of proteins in non-insulin dependent and insulin-dependent diabetes mellitus; impaired glucose tolerance; and obesity.

BACKGROUND OF THE INVENTION

Non-insulin dependent diabetes mellitus, or NIDDM, and Type II diabetes are synonymous. NIDDM patients have an abnormally high blood glucose concentration when fasting and delayed cellular uptake of glucose following meals or after a diagnostic test known as the glucose tolerance test. NIDDM is diagnosed based on recognized criteria (American Diabetes Association, Physician's Guide to Insulin-Dependent (Type I) Diabetes, 1988; American Diabetes Association, Physician's Guide to Non-Insulin-Dependent (Type II) Diabetes, 1988).

Insulin-Dependent diabetes mellitus, IDDM, and Type I diabetes are synonymous. IDDM patients have an abnormally high blood glucose concentration when fasting and delayed cellular uptake of glucose following meals or after a diagnostic test known as the glucose tolerance test. IDDM is diagnosed based on recognized criteria (American Diabetes Association, Physician's Guide to Insulin-Dependent (Type I) Diabetes, 1988).

Impaired glucose tolerance occurs when the rate of metabolic clearance of glucose from the blood is less than that commonly occurring in the general population after a standard dose of glucose has been orally or parenterally administered (American Diabetes Association, Physician's Guide to Non-Insulin-Dependent (Type II) Diabetes, 1988). Impaired glucose tolerance can occur in NIDDM, IDDM, gestational diabetes and obesity. Impaired glucose tolerance can also occur in individuals not meeting the diagnostic criteria for these disease states. Impaired glucose tolerance in non-diabetic individuals is a predisposing factor for the development of NIDDM.

Obesity is a condition in which there is an increase in body fat content resulting in excess body weight above the accepted norms for age, gender, height, and body build (Bray, Obesity, An Endocrine Perspective, p. 2303, Multihormonal Systems and Disorders (1989)). Accepted norms have been determined by life insurance mortality experience and by incidence of morbidity in relation to body composition. The excess mortality that occurs in obese individuals results from diseases that are predisposed by this condition. They include cancer, cardiovascular disease, digestive disease, respiratory disease and diabetes mellitus.

In patients with chronic hyperglycemia such as occurs in non-insulin dependent diabetes and insulin-dependent diabetes, glucose-dependent protein crosslinking occurs at a rate in excess of the norm (Bunn, American Journal of Medicine, Vol. 70, p. 325, 1981) resulting in altered tertiary protein structure (Brownlee, Chapter 18, Diabetes Mellitus, p. 279, 1990). Excessive non-enzymatic glycosylation of proteins contributes to diabetic complications and complications of aging in non-diabetic humans, such as neuropathy, nephropathy, retinopathy, hypertension, and atherosclerosis (Brownlee, 1990, supra).

Hyperglycemia is defined as blood glucose concentration in excess of the accepted norm for the general population (American Diabetes Association, Physician's Guide to Non-Insulin-Dependent (Type II) Diabetes, 1988).

While the relationship between these conditions is known, it would be an advantage to have a drug which can treat or prevent all of them.

INFORMATION DISCLOSURE 3-(1-(Aminomethyl)hydrazino)) propanoic acid is reported in JP 54128523 (Chem. Abstr. 92:75899h) to be a fungicide and insecticide. The synthesis of N-(hydrazinoiminomethyl)-glycine is reported in: Gante, J. Chem. Ber. 1968, 101, 1195. Certain alkylide-amino guanidine derivatives are described in U.S. Pat. No. 5,272,165 titled "Inhibiting advanced glycosylation of body proteins— using 2-alkylidene-amino:guanidine deriv., used e.g. for treating diabetic side-effects or esp. preventing tooth staining." Aminoguanidine analogs of arginine are disclosed in DE 4244539-A1 and WO 9104-023-A. U.S. Pat. No. 5,132,453 discloses that N6-(hydrazino:imino:methyl)-lysine is useful as an inhibitor of nitric oxide formation and for treating hypertension. EP-230-037-A discloses certain new 2-substituted-guanidine derivatives having antiischaemic and cardioprotective activity. U.S. Pat. No. 3,412,105 discloses β-Aryl-N-guanidino-(β-alanines or α-carboxy-β-alanines) as MAO inhibitors nd long acting hypotensives.

SUMMARY OF THE INVENTION

The present invention particularly provides:

(1) A compound of the formulae I or II:

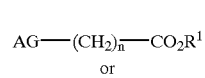

or

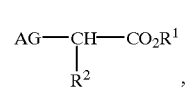

or a pharmacologically acceptable salt thereof,
wherein AG is
  a) N-aminoguanidine,
  b) N,N'-diaminoguanidine, or
  c) N,N',N''-triaminoguanidine;
wherein n is an integer from 1-5;
wherein $R^1$ is
  a) hydrogen,
  b) phenyl,
  c) $C_1$–$C_5$ alkyl, or
  d) $C_1$–$C_3$ alkyl-phenyl; and
wherein $R^2$ is
  a) hydrogen,
  b) phenyl,
  c) $C_1$–$C_{10}$ alkyl, or
  d) $C_1$–$C_5$ alkyl-phenyl
with the following provisos:
  a) in Formula II, when n is 2, $R_1$ is other than hydrogen;
  b) in Formula II, when n is one, $R_1$ is other than methyl;
  c) in Formula I, when $R_2$ is ethyl, $R_1$ is other than hydrogen;

d) in Formula I, when $R_2$ is phenyl, $R_1$ is other than hydrogen; and e) in Formula II, when n is 3, $R_1$ is other than hydrogen.

(2) a method for treating or preventing non-insulin dependent diabetes mellitus in a patient susceptible to or experiencing said NIDDM comprising the systemic administration of an amount effective to treat or prevent NIDDM of a compound of the formula III

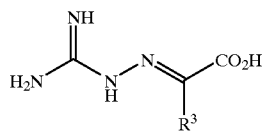

wherein $R^3$ is hydrogen, methyl, ethyl, $CH_2$phenyl, or n-hexyl.

For the generic formulae I and II, attachment of the AG fragment is unspecified, i.e. bonding to the adjacent carbon may occur at any one of the nitrogens of the AG fragment. The remaining nitrogens of the AG fragment are unsubstituted.

The carbon atom content of the carbon containing moieties is indicated by a prefix "$C_i$–$C_j$" wherein i is the lowest number of carbon atoms and j is the highest number of carbon atoms.

Examples of alkyl groups having from 1 to 10 carbon atoms include, for example, methyl, ethyl, n-propyl, isopropyl, n-butyl, isobutyl, t-butyl, n-pentyl, isoamyl, n-hexyl, n-heptyl, n-octyl, n-nonyl, n-decyl, and other isomeric forms thereof.

Examples of pharmaceutically acceptable acid addition salts include: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, 3-phenylpropionate, picrate, pivalate, propionate, succinate, tartrate, thiocyanate, tosylate, and undecanoate.

The dose of compounds of formula I–III to be used is between 0.1 and 100 mg/kg body weight daily. The preferred dose is 1–50 mg/kg/day. Administration may be by oral, parenteral, intranasal, buccal, sublingual, intrarectal, or transdermal routes. The oral route is preferred.

Novel compounds of the invention are given by the generic formulae I and II. Known compounds claimed for use in the treatment of NIDDM are represented by formula III.

Of the compounds of this invention, represented by generic formulae I and II, the compounds listed in Table 1 are especially preferred and their preferred utility is in the treatment of NIDDM and its complications.

Table 2 contains a list of related compounds which are not claimed. They are included to demonstrate the surprising effect of the claimed compounds by showing that these compounds, which are closely related to the claimed compounds, are not considered active at the highest dose tested.

Table 3 contains a list of compounds within the generic scope embodied in the generic formulae I and II which failed to exhibit activity at the highest dose tested and thus constitute exceptions, as seen by the provisos in claim 1.

Table 4 contains a list of novel compounds specifically claimed within the invention. Procedures for their preparation are given in Section 4.

Table 5 contains a list of known compounds being claimed for use in the treatment of NIDDM.

Thus, the present invention provides novel and known compounds having surprising and unexpected antidiabetic properties.

Administration of the compounds of this invention to KKAy mice at a dose of approximately 100–500 mg/kg/day results in the partial or complete amelioration of hyperglycemia in this rodent model of non-insulin dependent diabetes mellitus (Specific compounds are listed in Tables 4 and 5; see Chang, Wyse, Copeland, Peterson, and Ledbetter, Diabetes 1985, p. 466, 1986). KKAy mice are insulin resistant (Chang, et al, supra) and the finding that the non-fasting blood glucose level is reduced in these animals indicates that insulin resistance is most probably less after treatment with the claimed compounds. KKAy mice are obese compared to normal, outbred mice (Chang, et al, supra) and administration of compounds of the invention results in weight loss.

Administration of N-(dihydrazinomethylene)-glycine, the preferred compound in this series, to diabetic KKAy mice for 4 days decreased the non-fasting blood glucose level of the animals (see Table 6). A dose of 60 mg/kg/day produced a 35% decrease in the blood glucose level that was statistically significant compared to the control. Higher doses produced still greater reductions in the blood glucose concentration. 3-Guanidinopropionic acid at 500 mg/kg/day produced an approximately similar reduction in blood glucose concentration as was achieved with 60 mg/kg/day of the N-(dihydrazinomethylene)-glycine.

Administration of N-(dihydrazinomethylene)glycine to diabetic KKAy mice for 4 days decreased the body weight of the animals (see Table 6). A dose of 100 mg/kg/day produced a 4% decrease in the body weight that was statistically significant compared to the control. Higher doses produced a still greater reduction in the excess body weight of KKAy mice. 3-Guanidinopropionic acid at 500 mg/kg/day produced an approximately similar reduction in the body weight of KKAy mice as was achieved with 100 mg/kg/day of the N-(dihydrazinomethylene)-glycine.

Administration of N-(dihydrazinomethylene)-glycine to normal C57BL mice at 100 mg/kg decreased the fasting blood glucose concentration of these animals (Table 7).

Administration of N-(dihydrazinomethylene)-glycine to diabetic KKAY mice or normal C57BL mice at 100 mg/kg results in improved glucose tolerance as shown by lower blood glucose levels after injection of a standard test dose of glucose (Table 7).

Non-enzymatic glycosylation of proteins is the initial step in glucose-dependent crosslinking of proteins (Brownlee, supra). Non-enzymatic glycosylation of human serum albumin is reduced by N-(dihydrazinomethylene)-glycine, N-(hydrazinoiminomethyl)-glycine, and [2-(aminoiminomethyl)hydrazino]-, monohydrochloride acetic acid in vitro (Table 8). Aminoguanidine, which has previously been shown to inhibit non-enzymatic glycosylation of proteins in vitro (Khatami, Suldan, David, Li, and Rockey, Life Sciences, vol. 43, p. 1725–1731, 1988) and in vivo (Brownlee, supra), is also effective in this assay (Table 8). 3-Guanidinopropionic acid had no effect on non-enzymatic glycosylation of albumin in this assay.

In patients with diabetes mellitus, there are several metabolic disorders that would be of therapeutic benefit to correct: the abnormally elevated blood level of glucose in the fed and fasted states, the delayed clearance of glucose from the blood stream (American Diabetes Association, Physician's Guide to Insulin-Dependent (Type I) Diabetes, 1988; American Diabetes Association, Physician's Guide to Non-Insulin-Dependent (Type II) Diabetes, 1988), and the excessive glycosylation of proteins which contributes to the development of diabetic complications (Brownlee, supra). Furthermore, obesity is frequently associated with non-insulin dependent diabetes mellitus and aggravates the disordered glucose metabolism in these patients (Horton and Jeanrenaud, Chapter 27, Obesity and Diabetes Meliltus, 1990). The optimal treatment for non-insulin dependent diabetes mellitus would correct all of these disorders. Excessive glycosylation of proteins, such as can occur in non-insulin dependent diabetes mellitus and insulin-dependent diabetes mellitus patients, can be prevented by blocking the chemical reaction of glucose and protein molecules (Brownlee, supra) and reducing the abnormal elevation of blood glucose concentration in the diabetic state (Holman and Turner, Diabetic Medicine, 5:582–588, 1988; Benjamin and Sacks, Clin Chem., 4015:683–687, 1994). The most desirable treatment would act by both methods so as to more completely reduce the rate of non-enzymatic protein glycosylation.

It is the ability of the claimed compounds to positively effect multiple metabolic defects comprising diabetes mellitus and to prevent metabolic defects by more than one mechanism that clearly distinguishes their pharmacologic actions from other guanidine compounds that have previously been claimed as treatments for diabetes mellitus. The claimed compounds are unexpectedly superior to aminoguanidine, diaminoguanidine, 3-guanidinopropionic acid, and metformin in the treatment of NIDDM because they offer a more complete spectrum of desirable activities and are effective in lower doses.

The claimed compounds offer unexpected advantages in the treatment of diabetes mellitus compared to diaminoguanidine and aminoguanidine since the claimed compounds act metabolically to reduce excessive blood glucose concentration as well as directly blocking non-enzymatic glycosylation of proteins. The claimed compounds are unexpectedly superior to aminoguanidine and diaminoguanidine in the treatment of impaired glucose tolerance or obesity since aminoguanidine and diaminoguanidine lack efficacy in this regard. Aminoguanidine and diaminoguanidine inhibit non-enzymatic glycosylation of proteins in vitro and the formation of advanced glycosylation endproducts in vivo (Kumari, Umar, Bansal, and Sahib, Diabetes, 40:1079–1084, 1991). Based on its inhibition of non-enzymatic protein glycosylation, aminoguanidine has been suggested to have utility in the treatment of diabetes (Brownlee, supra). Aminoguanidine has no effect on the blood glucose level of normal rodents or rats made diabetic by injection of alloxan or streptozotocin (Kumari, Umar, Bansal, Sahib, supra; Yagihashi, Kamijo, Baba, Yagihashi, and Nagai, Diabetes, 41:47–52, 1992; Edelstein and Brownlee, Diabetologia, 35:96–97, 1992; Oxlund and Andreassen, Diabeterologia, 35:19–25, 1992). Diaminoguanidine has no effect on the blood glucose level of normal or alloxan-diabetic rats (Kumari, Umar, Bansal, Sahib, supra). Aminoguanidine has no effect on the body weight of normal or diabetic rats (Kumari, Umar, Bansal, Sahib, supra; Yagihashi, Kamijo, Baba, Yagihashi, and Nagai, supra; Oxlund and Andreassen, Diabetologia, 35:19–25, 1992) or results in an increase in body weight of human and rats (Baylin, Horakova, and Beaven, Experientia, 31:562, 1975). Diaminoguanidine does not affect the body weight of normal or alloxan-diabetic rats (Kumari, Umar, Bansal, Sahib, supra). An effect by aminoguanidine or diaminoguanidine on glucose tolerance has yet to be demonstrated.

The claimed compounds are unexpectedly superior to 3-guanidinopropionic acid in the treatment of diabetes mellitus since the latter is less potent in the control of hyperglycemia and lacks the ability to inhibit the non-enzymatic glycosylation of proteins. The claimed compounds are unexpectedly superior to 3-guanidinopropionic acid in the treatment of impaired glucose tolerance or obesity because of the greater potency of these compounds. 3-Guanidinopropionic acid has previously been shown to reduce hyperglycemia and excess body weight and to improve glucose tolerance in diabetic rodents (Meglasson, Wilson, Yu, Robinson, Wyse, and de Souza, J. Pharm. and Exp. Therapeutics, 266:1454–1462, 1993). The preferred compound in this claim, N-(dihydrazinomethylene)-glycine, is more potent than 3-guanidinopropionic acid in reducing the abnormally elevated blood glucose level and body weight of KKAy mice. To reduced the blood glucose level of KKAy mice by 20% required 130 mg/kg/day of the latter compound. A similar reduction in the blood glucose level could be achieved with a dose of 30 mg/kg/day of N-(dihydrazinomethylene)-glycine. N-(dihydrazinomethylene)-glycine administered to KKAy mice at 60 mg/kg/day was approximately as effective as 500 mg/kg/day of 3-guanidinopropionic acid. 3-Guanidinopropionic acid improves glucose tolerance in diabetic KKAy mice when administered in the chow as a 1% admixture which would deliver a dose of approximately 1000 mg/kg/day (U.S. Pat. No. 5,132,324). By comparison, N-(dihydrazinomethylene)-glycine improved the glucose tolerance of normal C57BL and diabetic KKAy mice when administered at 100 mg/kg/day. With respect to reducing body weight, 100 mg/kg/day of N-(dihydrazinomethylene)-glycine was approximately as effective as 500 mg/kg/day of 3-guanidinopropionic acid. 3-Guanidinopropionic acid does not inhibit non-enzymatic glycosylation of albumin in vitro in contrast to the claimed compounds.

The claimed compounds are unexpectedly superior to metformin in the treatment of diabetes mellitus, glucose intolerance, and obesity since the latter is less potent when tested in the same animal model as the claimed compounds. Also, with respect to its efficacy in reducing body weight and preventing non-enzymatic protein glycosylation, the disclosed data for metformin are contradictory and do not reveal a consistent result. Metformin has previously been shown to reduce hyperglycemia in non-insulin dependent diabetic patients when administered at 1000–3000 mg/day and to increase the rate of glucose clearance in such patients when administered at 1500–2500 mg/day (Bailey, Diabetes Care, 15:755–772, 1992). Rodents are less sensitive to metformin than humans and therefore higher doses (based on body weight) are required to demonstrate glycemic effects (Bailey, Flatt, Wilcock, and Day, Frontiers in Diabetes Research, pp. 277–282, 1990; Penicaud, Hitier, Ferre, and Girard, Biochem. J. 262:881–885, 1989). Chronic oral administration of metformin reduces hyperglycemia when administered to neonatal streptozotocin-diabetic rats at 100 mg/kg/day (Rossetti, DeFronzo, Gherzi, Stein, et al, Metabolism, 39:425–435, 1990), to DBM mice at 400 mglkg/day (Bailey, Flatt, Wilcock, and Day, supra), to Zucker fa/fa rats at 350 mg/kg/day (Penicaud, Hitier, Ferre, and Girard, supra), and to KKAy mice at 300 mg/kg/day or more (Meglasson, Wilson, Yu, Robinson, de Souza, supra). Chronic oral administration of metformin did not affect the blood glucose concentration in normal mice receiving 250 mg/kg/day, in streptozotocin-diabetic mice receiving 250 mg/kg/day (Bailey, Flatt, Wilcock, and Day, supra), or diabetic ob/ob mice receiving 250 mg/kg/day (Bailey, Flatt, and Ewan, Arch. Int. Pharmacodyn., 282:233–239, 1986). Acute administration of 264 mg/kg metformin or its analog buformin at 132 mg/kg did not affect the blood glucose level of rats (Tutwiler and Bridi, Diabetes, 27:868–876, 1978). When the preferred compound in this claim, N-(dihydrazinomethylene)-glycine was tested in KKAy mice it was more potent than metformin in reducing the abnormally elevated blood glucose level in this model. To reduce the blood glucose level of KKAy mice by 25% required 300 mg/kg/day of metformin (Meglasson, Wilson, Yu, Robinson, Wyse, and de Souza, supra). A similar reduction in the blood glucose level could be achieved with a dose of 30–60 mg/kg/day of N-(dihydrazinomethylene)-glycine. With respect to increasing glucose tolerance metformin has been reported to not affect glucose tolerance in normal rats when given at a dose of 750 mg/kg (Tutwiler and Bridi, supra) or in normal mice when given at 50 mg/kg (Bailey, Flatt, Wilcock, and Day, supra). When given to normal mice or streptozotocin-diabetic rats at 250 mg/kg oral glucose tolerance was increased (Bailey, Flatt, Wilcock, and Day, supra). By comparison, N-(dihydrazinomethylene)-glycine increased glucose tolerance when administered to normal C57BL or diabetic KKAy mice at a lower dose, 100 mg/kg. With respect to reducing body weight, metformin has been reported to cause weight loss in non-insulin dependent diabetic patients treated for one year (Bailey, supra) or to have no significant effect on the body weight of obese non-insulin dependent diabetic patients treated for a similar length of time (Multi-centre Study, Diabetologia, 24:404–411, 1983). Metformin did not cause weight loss in diabetic ob/ob mice when administered at 240 mg/kg/day or streptozotocin-diabetic mice when administered at 60 mg/kg/day (Lord, Atkins, and Bailey, Diabetologia 25:108–113, 1983). Metformin caused statistically significant weight loss in KKAy mice treated with 1700 mg/kg/day of the compound, but not when lower doses were given (Meglasson, Wilson, Yu, Robinson, Wyse, and de Souza, supra). By comparison, when N-(dihydrazinomethylene)-glycine was administered to KKAy mice at 100 mg/kg/day it was approximately as effective as 1700 mg/kg/day of metformin in producing weight loss in this obese mouse strain (Meglasson, Wilson, Yu, Robinson, Wyse, and de Souza, supra). Metformin has been reported to inhibit non-enzymatic glycosylation of erythrocyte plasma membranes at concentrations of 0.5 and 5 micromoles per liter based on its ability to prevent the decrease in the electron paramagnetic resonance spectroscopy order parameters of plasma membranes incubated with glucose in vitro (Freisleben, Ruckert, Wiernsperger, and Zimmer, Biochemical Pharmacology, 43:1185–1194, 1992). At higher concentrations, 50 and 100 micromoles per liter, metformin had the reverse effect and caused a very low order parameter. Hence, whether metformin could be expected to lessen or aggravate non-enzymatic glycosylation of proteins in diabetic patients would depend on the concentration of metformin in serum of treated patients. In diabetic humans administered 1 gram of metformin orally, the average Cmax plasma concentration is 3.24 micrograms per milliliter (or 25 micromoles per liter) (Tucker, Casey, Phillips, Connor, et al., Br. J. Clin. Pharmacol., 2:235–246, 1981) and, therefore, lies midway between the highest concentration shown to reduce non-enzymatic glycosylation of erythrocytes and the lowest concentration shown to stimulate the process. Based on the published metformin plasma levels in diabetic patients no conclusion can be drawn as to whether metformin would inhibit the non-enzymatic glycosylation of proteins or aggravate the process in some manner when administered as a therapy to patients.

General methods for the preparation of the compounds of this invention are outlined in Schemes 1–4. Specific examples for a number of these techniques can be found in the experimental procedures presented in the Description of the Preferred Embodiment. By using other starting materials and reactants the various compounds of the invention may be prepared. The following references discuss procedures relating to the general syntheses of the compounds of this invention.

Scheme 1: Gante, J. Chem. Ber. 1968, 101, 1195. Armarego, W. L. F.; Kobayashi, T. J. Chem. Soc. (C) 1971, 238. Evans, D. A.; Britton, T. C.; Dorow, R. L.; Dellaria, J. F. J. Am. Chem. Soc. 1986, 108, 6395. Evans, D. A.; Britton, T. C.; Dorow, R. L.; Dellaria, J. F. Tetrahedron 1988, 44, 5525.

Scheme 3: Gut, J.; Hesoun, D.; Novacek, A. Coll. Czech. Chem. Comm. 1966, 31, 2014. Miura, K.; Ikeda, M.; Kondo, T.; Setogawa, K. Chem. Abstr. 1962, 56:4767b. Pankaskie, M.; Abdel-Monem, M. M. J. Pharm. Sci. 1980, 69, 1000.

Scheme 4: Lee, K; Kim, S.; Um, H.; Park, H. Synthesis 1989, 638. Reddy, T. I.; Bhawal, B. M.; Rajappa, S. Tetrahedron 1993, 49, 2101. In Vivo and In Vitro Screening Protocols.

DESCRIPTION OF THE PREFERRED EMBODIMENTS

The following experimental procedures are specific examples which describe the preparation of a number of compounds of the invention:

EXAMPLE 1

[2-(aminoiminomethyl)hydrazino]-acetic acid

Ethylhydrazinoacetate hydrochloride (7.73 g, 50 mmol) was saponified by refluxing in 100 mL of 1N NaOH for 2 h. To the hot solution was then added 2-methyl-2-thiopseudourea sulfate (6.95 g, 50 mmol) and the solution was refluxed for an additional 2 h. The mixture was concentrated to ~½ volume at which time a white solid precipitated. The solution was cooled and filtered to yield 3.34 g of a white solid. Recrystallization from water afforded 2.41 g (36%) of [2-(aminoiminomethyl)hydrazino]-acetic acid as a highly crystalline white solid. MP: 247–248° C. (dec); $^1$H NMR: (D$_2$O) δ 3.40 (s, 2H).

EXAMPLE 2

[2-(aminoiminomethyl)hydrazino]-, monohydrochloride acetic acid

To a stirring solution of [(aminoiminomethyl) hydrazono]-, monohydrochloride, monohydrate acetic acid (10 g, 60 mmol) in methanol (300 ml) was added 10% Pd-C (0.25g) and the mixture hydrogenated at 30 psi overnight. The mixture was filtered and solvent evaporated to dryness. The residue was recrystallized from EtOH to afford 4.2 g (42%) title compound as a white solid (m.p. 163–165° C.). $^1$H NMR (D$_2$O) δ 3.68 (s, 2H).

EXAMPLE 3

[2-(aminoiminomethyl)hydrazino] acetic acid phenylmethyl ester monohydrochloride]

HCl (g) was bubbled through a suspension of [2-(aminoiminomethyl)hydrazino]-acetic acid (2.00 g, 15.2 mmol) in benzyl alcohol (30 mL). The reaction was stirred for about an hour until everything was in solution. The crude product was precipitated out by adding $Et_2O$. This material was recrystallized from MeOH/EtOAc to yield [2-(aminoiminomethyl)hydrazino] acetic acid phenylmethyl ester monohydrochloride (3.20 g, 82%) as a white crystalline solid. MP: 162–164 °C. $^1H$ NMR ($CD_3OD$): δ 3.69 (s, 2H), 5.24 (s, 2H), 7.34–7.42 (m, 5H).

EXAMPLE 4
α-hydrazinobenzenepropanoic acid

A solution of LDA (50 mL of a 1.5M solution in THF) in 250 mL of dry THF was cooled to −78° C. To this was added dropwise a solution of ethylhydrocinnamate (12.0 mL, 68.2 mmol) in 250 mL dry THF. The solution was stirred at −78° C. for 30 min. A solution of di-tert-butyl azodicarboxylate (18.84 g, 81.8 mmol) in 100 mL dry THF was then added dropwise. After 10 min, the reaction was quenched by the addition of 14 mL HOAc and allowing to warm to room temperature. The mixture was partitioned between $Et_2O$ and water. The aqueous layer was extracted with $Et_2O$ (3×100 mL). The combined organic layers were washed with saturated aq $NaHCO_3$ (2×100 mL) and brine (1×100 mL), dried over sodium sulfate and condensed. The crude product was chromatographed on silica (90/10 hexane/EtOAc) to afford 15.33 g (55%) of the bis-BOC protected hydrazino ester. The ester was taken up in 200 mL $CH_2Cl_2$. To this was added 120 mL of trifluoroacetic acid. The mixture was stirred 2 h at room temperature. After removal of the solvent, the crude product was taken up in 75 mL of 1N NaOH and refluxed for 2 h. The solution was cooled, extracted with $Et_2O$, neutralized, condensed to half volume, cooled and filtered. The resulting brownish solid was stirred in boiling i-PrOH for 5 min to remove colored impurities. Filtration and drying yielded 3.35 g (27%) of α-hydrazinobenzenepropanoic acid as a white solid. MP: 198–201° C. (dec). $^1H$ NMR: ($D_2O$) δ 7.41–7.29 (m, 5H), 3.89 (dd, J=7, 6 Hz, 1H), 3.23–3.08 (m, 2H).

EXAMPLE 5
α-[2-(aminoiminomethyl)hydrazino]benzenepropanoic acid monohydrate]

A solution of α-hydrazinobenzenepropanoic acid (3.00 g, 16.7 mmol) and 2-methyl-2-thiopsuedourea sulfate (2.55 g, 18.3 mmol) in 17 mL 1N NaOH was heated to reflux for 2 h. The mixture was neutralized with 3N HCl and concentrated until precipitation began (ca. ½ volume). The crude product was filtered and recrystallized from water to yield 1.81 g (49%) of α-[2-(aminoiminomethyl)hydrazino] benzenepropanoic acid monohydrate as a monohydrate. MP: 127–130° C. (dec). $^1H$ NMR: ($D_2O$) δ 7.40–7.27 (m, 5H), 3.60 (dd, J=8, 6 Hz, 1H), 3.04 (dd, J=14, 6 Hz, 1H), 2.86 (dd, J=14, 8 Hz, 1H). 2-[2-(Aminoiminomethyl)hydrazino] propanoic acid.

A mixture of 10.0 g (55.4 mmol) 2-[(aminoiminomethyl) hydrazono]propanoic acid hydrochloride (J. Pharmaceut. Sci. 1980, 69, 1000–1004), 1.5 g of 10% palladium on carbon, and 300 mL of distilled water was shaken under 50 psi hydrogen pressure for 16 h at 25° C. The mixture was filtered. To the filtrate was added 75 g of Dowex IR118H hydrogen form strongly acidic cation exchange resin. The mixture was stirred 1 hour and then the mixture was filtered. The resin was washed with three 150 mL portions of distilled water. The combined filtrate and washes were discarded and the resin was washed with five 200 mL portions of 20% (vol./vol.) pyridine in distilled water. These washes were combined and the solvent was evaporated at reduced pressure (25° C., 1 torr). The resulting white powder was dissolved in 30 mL of refluxing distilled water and the resulting solution was diluted with 90 mL of hot absolute ethanol. The mixture was allowed to cool to 25° C., and after 24 h the precipitate which formed was collected by filtration. The solid was dried (20 torr/50° C./24 hours) to give 3.8 g of the title compound as a white solid, mp 239–241° C.

EXAMPLE 6
[1-(aminoiminomethyl)hydrazino] acetic acid monohydrobromide

To a stirring suspension of aminoguanidine bicarbonate (100 g, 734 mmol) in water (200 ml) was added bromoacetic acid (100 g, 720 mmol). After initial effervescence the homogeneous solution was refluxed overnight, cooled to ambient temperature, and solvent evaporated to dryness. The residue was suspended in EtOH (200 ml) and sonicated. the solid was filtered to afford 13.6 g (9%) of title compound as a white solid (m.p. 163–165° C.). $^1H$ NMR ($D_2O$) δ 4.25 (s, 2H).

EXAMPLE 7
3-[[imino[(1-methylethylidene)hydrazino]methyl]amino] propanoic acid β-alanine (6.00 g, 67.5 mmol) was dissolved in 67.5 mL of 1N NaOH. To this was added N-amino-S-methylisothiourea hydroiodide (15.69 g, 67.5 mmol). The mixture was heated to reflux for 1.5 h. The solvent was removed. The crude product was taken up in ca. 50 mL water and 50 mL of acetone was added. Removal of the solvent afforded an orange solid which was chromatographed on silica (80/20 $CHCl_3$/MeOH then 60/40 $CHCl_3$/MeOH) to yield 5.88 g (47%) of 3-[[imino[(1-methylethylidene) hydrazino]methyl] amino]propanoic acid as a pale orange solid. MP: ~125° C. (dec). $^1H$ NMR: ($D_2O$) δ 3.36 (t, J=6 Hz, 2H), 2.35 (t, J=6 Hz, 2H), 1.87 (s, 3H), 1.80 (s, 3H).

EXAMPLE 8
N-(hydrazinoiminomethyl)-β-alanine

3-[[imino[(1-methylethylidene)hydrazino]methyl]amino] propanoic acid (5.88 g, 31.61 mmol) was dissolved in 125 mL water and heated to 60° C. for 72 h. The solvent was evaporated and the product was stirred in a 4:1 mixture of EtOH and MeOH. The resulting pale orange precipitate was filtered, washed with ethanol and dried to yield 3.16 g (68%) of N-(hydrazinoiminomethyl)β-alanine as a pale orange solid. MP: 177–179° C. $^1H$ NMR: ($D_2O$) δ 3.39 (t, J=6 Hz, 2H), 2.42 (t, J=6Hz, 2H).

EXAMPLE 9
N-(dihydrazinomethylene)-1-alanine

To a suspension of L-alanine (10.0 g, 0.11 mol) and triethylamine (33.5 mL, 0.24 mol) in EtOH (90 ml) and $H_2O$ (6 mL) was added carbon disulfide (7.2 mL, 0.12 mol). After stirring overnight, methyl iodide (7.5 mL, 0.12 mol) was added to the yellow solution. The mixture was stirred for 1 h and concentrated to a slurry. The residue was dissolved in $H_2O$ (25 mL), and conc. HCl was added until acidic. The mixture was extracted with $Et_2O$ (3×100 mL), and the organic phase was dried ($MgSO_4$) and concentrated to provide 18.4 g (93%) of the corresponding dithiocarbamate as a pale yellow solid of good purity. A analytically pure sample was obtained by recrystallization from $Et_2O$/hexane: m.p. 90–92; $^1H$ NMR ($D_2O$) δ 4.89 (q, J=7 Hz, 1 H), 2.59 (s, 3 H), 1.52 (d, J=7 Hz, 3 H).

To a solution of the dithiocarbamate (5.0 g, 28 mmol) in methylene chloride (50 mL) at 0° C. was added methyl trifluoromethanesulfonate (3.5 mL, 31 mmol). The mixture was warmed to room temperature and stirred for 20 h. The mixture was concentrated under reduced pressure to a colorless oil. The resulting oil was dissolved in $H_2O$ (5 mL), and 1.0 M NaOH (28 mmol) was added. The mixture was extracted with EtOAc (3×100 mL), and the organic phase was dried ($MgSO_4$). After filtration, the solvent was removed in vacuo to provide a thick viscous oil. The oil was dissolved in absolute EtOH (25 mL), and anhydrous hydrazine (4.4 mL, 0.14 mol) was added. The mixture was stirred for 1.5 h, and the solid (2.5 g) which formed was collected by filtration. The white powder was further purified by crystallization from $H_2O$/IPA to give 2.2 g (49%) of the diaminoguanidine as a white powder: m.p. 174–176 (dec.); $^1$H NMR ($D_2O$) δ 3.69 (q, J=7 Hz, 1 H), 1.20 (d, J=7Hz, 3 H).

EXAMPLE 10
N-(dihydrazinomethylene)β-alanine

By a procedure analogous to that employed for N-(dihydrazinomethylene)-1-alanine, β-alanine was converted to N-(dihydrazinomethylene)-β-alanine (m.p. 192° C., dec.). $^1$H NMR ($D_2O$) 3.40 (t, 2H, J=7 Hz), 2.48 (t, 2H, J=7 Hz).

EXAMPLE 11
N-(dihydrazinomethylene)-glycine

A solution of methylated thiocarbohydrazide (25.0 g, 101 mmol) and glycine (6.314 g, 83.98 mmol) in water (50 mL) and 12.5 N NaOH (8.89 mL, 111 mmol) was stirred under nitrogen at 75–80° C. for 3 hrs. The solution was chilled in ice while still under nitrogen before the portionwise addition of abs. ethanol (550 mL in 50 mL portions), stirring between each addn until pptn was complete. The mixture was then stirred for 15 min. at 0° C. before filtering. The collected solid was washed thoroughly with abs. ethanol. Drying gave a lt. pink powder (8.04 g). The crude solid was dissolved in water (30 mL), filtered to remove some fine insoluble material, and then diluted to a volume of 250 mL with abs. ethanol. Precipitation began almost immediately and was accelerated by sonication for a few seconds. After standing at room temp for 10 min, the mixture was filtered, giving a pale rose powder (5.25 g, 42%, m.p. 200° C., dec.). $^1$H NMR ($D^2O$) 3.78 (s).

EXAMPLE 12
[2-(hydrazinoiminomethyl)hydrazino] acetic acid

Ethylhydrazinoacetate hydrochloride (9.28 g, 60 mmol) was saponified by refluxing in 120 mL of 1N NaOH for 2 h. To the hot solution was then added N-amino-S-methylisothiourea hydroiodide (13.98 g, 60 mmol) and the solution was refluxed for an additional 2 h. The solvent was removed. The crude product was dissolved in methanol and filtered to remove the NaCl. The filtrate was condensed and dried by high vac. The residue was then stirred with 150 mL MeOH overnight. The resulting white solid was filtered. This solid was then refluxed in 100 mL MeOH for 2 h to remove any impurities. The mixture was then cooled and filtered. The resulting solid was dried in vacuo to yield 2.14 g (24%) of [2-(hydrazinoiminomethyl)hydrazino] acetic acid as an off-white solid. MP: 201–203° C. (dec). $^1$H NMR: ($D_2O$) δ 3.39 (s, 2H).

EXAMPLE 13
N-(dihydrazinomethylene)-d-alanine

To a suspension of D-alanine (1.8 g, 20 mmol) and triethylamine (6.1 mL, 44 mmol) in EtOH (15 ml) and $H_2O$ (1 mL) was added carbon disulfide (1.3 mL, 22 mmol). After stirring overnight, methyl iodide (1.4 mL, 22 mmol) was added to the yellow solution. The mixture was stirred for 1 h and concentrated to a slurry. The residue was dissolved in $H_2O$, and conc. HCl was added until acidic. The mixture was extracted with methyl t-butyl ether (3×50 mL), and the organic phase was dried ($MgSO_4$) and concentrated to provide a yellow oil, which with sonication and the addition of a small amount of hexane solidified. Upon further drying, 2.9 g of a yellow solid was obtained. The product was further purified by recrystallization ($Et_2O$/hexane) to give 1.67 g (47%) of the compound identified as compound A of Table 9 as a cream solid: m.p. 89–91° C.; $^1$H NMR ($D_2O$) δ 4.67 (m, 1 H), 2.39 (s, 3 H), 1.32 (d, J=7.0 Hz, 3 H).

To a solution of the dithiocarbamate of Compound A of Table 9 (15.1 g, 84.3 mmol) in methylene chloride (170 mL) at 0° C. was added methyl trifluoromethanesulfonate (10.5 mL, 92.7 mmol). The mixture was warmed to room temperature and stirred for 20 h. The mixture was concentrated under reduced pressure to a colorless oil. The resulting oil was dissolved in $H_2O$ (40 mL), and 1.0 M NaOH (84.3 mmol) was added. The mixture was extracted with EtOAc (3×200 mL), and the organic phase was dried ($MgSO_4$). After filtration, the solvent was removed in vacuo to provide a thick viscous oil. The oil was dissolved in absolute EtOH (85 mL), and anhydrous hydrazine (13.2 mL, 0.42 mol) was added. The mixture was stirred for 1.5 h, and the solid (7.5 g) which formed was collected by filtration. The white powder was further purified by crystallization from $H_2O$/IPA to give 6.48 g (48%) of the title compound as a white powder: m.p. 175–177° C.; H NMR ($D_2O$) δ 3.69 (q, J=7 Hz, 1 H), 1.20 (d, J=7 Hz, 3 H).

EXAMPLE 14
N-(dihydrazinomethylene)-valine

To a suspension of L-valine (5.0 g, 42.7 mmol) and triethylamine (13.1 mL, 93.9 mmol) in EtOH (30 ml) and $H_2O$ (2 mL) was added carbon disulfide (2.8 mL, 47.0 mmol). After stirring overnight, methyl iodide (2.9 mL, 47.0 mmol) was added to the yellow solution. The mixture was stirred for 2 h and concentrated to a slurry. The residue was dissolved in $H_2O$ (10 mL), and conc. HCl was added until acidic. The mixture was extracted with $Et_2O$ (3×100 mL), and the organic phase was dried ($MgSO_4$) and concentrated to provide a yellow oil which after seeding gave a yellow solid. The solid was suspended in hexane and filtered to yield 7.7 g of Compound B of Table 9 as an off-white solid. The filtrate was cooled to 0° C. to yield a second crop of 0.27 g of Compound B of Table 9 (7.97 g total, 90%) as a white solid: m.p. 76–78° C.; $^1$H NMR ($CDCl_3$) δ 5.30 (m, 1 H), 2.40 (m, 1 H), 1.08 (d, J=7.0 Hz, 3 H), 1.04 (d, J=7.0 Hz, 3 H).

To a solution of Compound B of Table 9 (8.0 g, 38.6 mmol) in methylene chloride (60 mL) at 0° C. was added methyl trifluoromethanesulfonate (4.8 mL, 42.5 mmol). The mixture was warmed to room temperature and stirred for 20 h. The mixture was concentrated under reduced pressure to a colorless oil. The resulting oil was dissolved in $H_2O$ (10 mL), and 1.0 M NaOH (38.6 mL) was added. The mixture was extracted with EtOAc (3×100 mL), and the organic phase was dried ($MgSO_4$). After filtration, the solvent was removed in vacuo to provide a thick viscous oil. The oil was dissolved in isopropyl alcohol (150 mL), and hydrazine monohyrate (9.4 mL, 0.19 mol) was added. The mixture was stirred for 2 h, and THF was added which resulted in a more filterable solid. Filtration provided 2.4 g (33%) of the title compound as a slightly hygroscopic white solid: m.p. 112–116° C.; $^1$H NMR ($D_2O$) δ 3.70 (d, J=5.0 Hz, 1 H), 2.20 (m, 1 H), 0.97 (d, J=7.0 Hz, 3 H), 0.94 (d, J=7.0 Hz, 3 H).

EXAMPLE 15

[1-(aminohydrazonomethyl)hydrazino]acetic acid (Please refer to Scheme 5).

PREPARATION OF 9

To a stirring suspension of ethyl hydrazinoacetate hydrochloride (5.0 g, 32.34 mmol) and N-methyl morpholine (3.26 g, 32.34 mmol) at 0° C. was added solid N-(Benzyloxycarbonyloxy)succinimide (8.06 g, 32.34 mmol). The mixture was allowed to warm to ambient temperature overnight and the solvent removed in vacuo. The residue was suspended between EtOAc/H$_2$O, the layers shaken, the organics separated and dried over Na$_2$SO$_4$. The solvent was removed and the residue chomatographed via SiO$_2$ flash chromatography (eluant 4:1 hexane/EtOAc) to afford 5.7 g (70%) title compound as a white solid. m.p. 95–97° C. The residue in subsequent reactions was purified by recrystallization from EtOAc/hexane to afford title compound in slightly lower yield. $^1$H NMR (CDCl$_3$) δ 1.27 (t, J=7 Hz, 3 H), 3.66 (s, 2 H), 4.19 (q, J=7 Hz, 2 H), 5.13 (s, 2 H), 6.77 (brs, 1 H), 7.33 (m, 5 H).

PREPARATION OF 10

To a stirring suspension of Preparation 9 (3.0 g, 11.89 mmol) in EtOH (30 ml) at ambient temperature, was added aqueous NaOH (1N, 11.89 ml). To the mixture was added additional H$_2$O (10 ml) and stirred for 1 hr (The mixture became a homogeneous solution and then a solid precipitated). Aqueous HCl (1 N, 11.89 ml) was then added, the ethanol removed in vacuo and the aqueous extracted with EtOAc (2×100 ml). The organic layers were combined, dried over Na$_2$SO$_4$, and the solvent removed to afford 2.31 g (87%) title compound as white solid. m.p. 131–133° C. $^1$H NMR (CD$_3$OD) δ 3.59 (s, 2 H), 5.15 (s, 2 H), 7.37 (m, 5 H).

PREPARATION OF 11

To a stirring suspension of Preparation 10 (25.44 g, 112.7 mmol) in EtOAc (500 ml) was added trimethylsilyl isothiocyanate (14.79 g, 112.7 mmol) and the mixture was heated at gentle reflux (80° C.) overnight. The resulting solution was cooled to ambient temperature and washed with H$_2$O (2×100 ml). The organic layer was separated, dried over Na$_2$SO$_4$, and the solvent evaporated to dryness. The oily residue was dissolved in CH$_2$Cl$_2$ and allowed to stand at ambient temperature for 3 min in which time a solid forms. The solid was filtered, washed with CH$_2$Cl$_2$ (100 ml) and dried in vacuo. The solid was slurried in hot EtOAc (300 ml) to dissolve any sulphur related by-products and triturated with hexane (200 ml) to afford 17.1 g title compound (53%) as a white solid. m.p. 148–149° C. $^1$H NMR (CD$_3$OD) δ 5.20 (s,2 H), 7.30 (m, 5 H) remaining CH2 not observable.

PREPARATION OF 12

To a stirring solution of Preparation 11 (5.0 g, 17.64 mmol) in EtOH (150 ml) at ambient temperature was added methyl iodide (2.73 g, 19.41 mmol) and the resulting solution stirred overnight. The solvent was removed in vacuo to afford 7.50 g (quant) title compound as a yellow foam. $^1$H NMR (CD$_3$OD) δ 2.69 (brs, .6 H), 2.84 (brs, 0.4H), 4.40–4.70 (m, 2H), 5.31 (brs, 2H), 7.46 (m, 5H).

PREPARATION OF 13

To a vigorously stirring solution of Preparation 12 (25.5 g, 60 mmol) in H$_2$O (100 ml) at ambient temperature was added hydrazine hydrate (6.06 g, 120 mmol) slowly until ½ had been added. H$_2$O (10 ml) was added to the solid mass which had formed and the solids broken up mechanically with a spatula. The remaining hydrazine was then added and the solution vigorously stirred for 1 hour. The heterogeneous mixture was sonicated and stirring continued until a thick mass had formed. EtOH (50 ml) was added, the solid filtered, washed with EtOH and dried in vacuo to afford 9.24 g (55%) title compound as a white solid. m.p. 168–170° C. $^1$H NMR (D$_2$O) δ 3.86 (brs, 1 H), 4.21 (brs, 1 H), 5.17 (s, 2 H), 7.39 (s, 5 H). [1-(aminohydrazonomethyl)hydrazino] acetic acid.

To a solution of Preparation 13 (9.20 g, 32.71 mmol) in MeOH/H$_2$O (400 ml, ~2:1 v/v) was added 10% Pd-C (1.0 g) and the mixture hydrogenated at 30 psi for 4 hours. The catalyst was filtered through diatomaceous earth and 10% Pd-C (1.0 g) was again added. The mixture was hydrogenated at 30 psi for 2.5 hours and determined to be complete by TLC (eluant 85:14:1 CH$_2$Cl$_2$/MeOH/HCO$_2$H). The mixture was filtered through diatomaceous earth and solvent removed to ~50 ml at which time a solid precipitated. The solid was filtered, washed with a minimum amount of H$_2$O and dried in vacuo to afford 3.60 g (75%) title compound as an off white solid. m.p. 196–198° C. A second crop was obtained by concentrating the filtrate until a solid formed. Filtration afforded 0.90 g (19%, total yield: 94%) additional material having identical melting point. $^1$H NMR (D$_2$O) δ 4.06 (s, 2 H).

BIOLOGICAL TESTING

Compounds of the present invention were tested for their ability to reduce blood glucose and body weight as follows:

KKAy mice are rodent models of NIDDM and obesity (Chang, Wyse, Copeland, Peterson, and Ledbetter, 1986). A pre-treatment blood sample was obtained from the retroorbital sinus and the mice arranged in groups of 6 so that the mean pre-treatment blood glucose level was the same on average in all groups. Test compounds were admixed in the chow at a concentration of 0.5% and the mice were allowed to consume the diet ad libitum. Control mice received unsupplemented chow. On Day 0, the mice were weighed and provided control chow or chow supplemented with test compounds. After 3 days of consuming control chow or chow supplemented with test compounds, a blood sample was obtained for determination of the glucose concentration and the animals were weighed for determination of weight loss. Food consumption was measured by weighing the food provided at the beginning of the study and the food residue at the end of the study. Food consumption was calculated by subtracting the weight of the residue from the weight of the food provided. Drug intake was calculated by multiplying food consumption by 0.5%. Using this method drug intake was determined to be approximately 500 mg/kg/day. Blood glucose data are expressed as the average blood glucose concentration in the test group divided by the average blood glucose level in the control group (treatment/control or T/C). Compounds resulting in T/C values equal to or less than 0.90 are considered to be active anti-hyperglycemic agents. Weigh loss data are expressed as percent change in body weight. Compounds resulting in a decrease of 1% or more less than control in body weight over three days are considered to be active anti-obesity agents.

TABLE 1

Preferred Compounds of the Invention

| Structure | Name |
|---|---|
| H$_2$N—C(=NH)—NH—NH—CH$_2$—C(=O)—OH | Acetic acid, [2-(amino-iminomethyl)-hydrazino]— |

TABLE 1-continued

Preferred Compounds of the Invention

| Structure | Name |
|---|---|
| H₂N—C(=NH)—NH—NHCH₂—C(=O)—OH · HCl | Acetic acid, [2-(amino-iminomethyl)-hydrazino]-monohydrochloride |
| H₂N—NH—C(=NH)—NH—CH₂—C(=O)—OH | Glycine, N-(hydrazino-iminomethyl)— |
| H₂N—NH—C(=NH)—NH—CH₂—C(=O)—OH · 0.5 HCl | Glycine, N-(hydrazino-iminomethyl)—, hydrochloride (2:1) |
| H₂N—NH—C(=N—)(NH—NH₂)—... —CH₂—C(=O)—OH | N-(Dihydrazino-methylene)-glycine |
| H₂N—C(=N—NH₂)—NH—NHCH₂—C(=O)—OH | Acetic acid, [2-(hydrazinoiminomethyl-hydrazino]— |
| (NH₂)(NH₂)N—C(=NH)—N(H)—CH₂—C(=O)—OH | [1-(aminohydrazonomethyl)hydrazino]acetic acid |

TABLE 2

Related Inactive Compounds Which are not Claimed

| Structure | Name |
|---|---|
| H₂N—C(=NH)—N(CH₃)—N=CH—C(=O)—OH · 0.5 H₂SO₄ | Acetic acid, [(amino-iminomethyl)-methyl-hydrazono], sulfate (2:1) |
| H₂N—C(=N—NO₂)—NH—N=CH—C(=O)—OH | Acetic acid, [[imino-(nitroamino)-methyl]-hydrazono]— |
| H₂N—C(=N—CH₃)—NH—N=CH—C(=O)—OH | Acetic acid, [[imino-(methylamino)-methyl]-hydrazono]— |

TABLE 2-continued

Related Inactive Compounds Which are not Claimed

| Structure | Name |
|---|---|
| H—CH=N—NH—C(=NH)—NH—CH₂—C(=O)—OH | |
| O₂N—NH—C(=NH)—NH—CH₂—C(=O)—OH | |

TABLE 3

Inactive Exceptions to the Generic Scope

| Structure | Name |
|---|---|
| NH₂—C(=NH)—NH—NH—CH₂CH₂—C(=O)—OH | Propanoic acid, 3-[1-(aminoiminomethyl)-hydrazino]— |
| H₂N—C(=NH)—NH—NH—CH₂—C(=O)—OCH₃ | |
| H₂N—C(=NH)—NH—NH—CH(CH₃)—C(=O)—OH | Butanoic acid, 2-[2-(aminoiminomethyl)-hydrazino]— |
| H₂N—C(=NH)—NH—NH—CH(C₆H₅)—C(=O)—OH | |
| H₂N—C(=NH)—N(H)—CH₂CH₂CH₂—COOH (with NH—NH₂) | Butanoic acid, 4-[(hydrazinoiminomethyl)-amino]— |

TABLE 4

Specifically Claimed Compounds of the Invention

| Structure | Name |
|---|---|
| $H_2N-C(=NH)-NH-NH-CH_2-C(=O)-OH$ | Acetic acid, [2-(aminoiminomethyl)-hydrazino]— |
| $H_2N-C(=NH)-NH-NHCH_2-C(=O)-OH \cdot HCl$ | Acetic acid, [2-(aminoiminomethyl)-hydrazino]—, monohydrochloride |
| $H_2N-C(=NH)-NH-NH-CH_2-C(=O)-O-CH_2-C_6H_5 \cdot HCl$ | Acetic acid, [2-(aminoiminomethyl)-hydrazino]—, phenylmethyl ester, monohydrochloride |
| $H_2N-C(=NH)-NH-NH-CH(CH_2C_6H_5)-C(=O)-OH \cdot H_2O$ | Benzenepropanoic acid, alpha[2-(aminoiminomethyl)hydrazino], monohydrate |
| $H_2N-C(=NH)-N(H)-N(H)-CH(CH_3)-COOH$ (racemate) | |
| $H_2N-C(=NH)-N(NH_2)-CH_2-C(=O)-OH \cdot HBr$ | Acetic acid, [1-(aminoiminomethyl)-hydrazino]—, monohydrobromide |
| $H_2N-C(=N-NH_2)-NH-CH_2CH_2-C(=O)-OH$ | β-Alanine, N-(hydrazinoiminomethyl)— |
| $H_2N-N(H)-C(=N-CH_2-C(=O)-OH)-NH-NH_2$ | N-(Dihydrazinomethylene)-glycine |
| $H_2N-C(=N-NH_2)-NH-NHCH_2-C(=O)-OH$ | Acetic acid, [2-(hydrazinoiminomethyl)-hydrazino]— |
| $H_2N-N(H)-C(=N-CH_2CH_2-COOH)-NH-NH_2$ | β-Alanine, N-(dihydrazinomethylene)— |

TABLE 4-continued

Specifically Claimed Compounds of the Invention

| Structure | Name |
|---|---|
| H2N-NH-C(=N-)-NH-NH2 with =N-CH(CH3)-COOH (L config) | L-Alanine, N-(dihydrazinomethylene)— |
| H2N-NH-C(=N-)-NH-NH2 with =N-CH(CH3)-COOH (D config) | N-(dihydrazinomethylene)-d-alanine |
| H2N-NH-C(=N-)-NH-NH2 with =N-CH(CH(CH3)2)-COOH | N-(dihydrazinomethylene)-valine |
| H-NH-N(NH2)-C(=NH)-N(NH2)-CH2-C(=O)-OH | [1-(aminohydrazonomethyl)hydrazino]acetic acid |

TABLE 5

Known Compounds Claimed for Treatment NIDDM

| Structure | Name |
|---|---|
| H2N-C(=NH)-NH-N=CH-C(=O)-OH · H2O · HCl | Acetic acid, [(aminoiminomethyl)hydrazono]—, monohydrochloride, monohydrate |
| H2N-C(=NH)-N(H)-N=C(CH3)-COOH · HCl | Propanoic acid, 2-[(amino-iminomethyl)hydrazono]—, monohydrochloride |
| H2N-C(=NH)-N(H)-N=C(CH2CH3)-COOH · HCl | Butanoic acid, 2-[(amino-iminomethyl)hydrazono]—, monohydrochloride |
| H2N-N(H)-C(=NH)-N(H)-CH2-C(=O)-OH | Glycine, N-(hydrazinoiminomethyl)— |
| H2N-N(H)-C(=NH)-N(H)-CH2-C(=O)-OH · 0.5 HCl | Glycine, N-(hydrazinoiminomethyl)—, hydrochloride (2:1) |

TABLE 5-continued

Known Compounds Claimed for Treatment NIDDM

| Structure | Name |
|---|---|
| (structure with guanidinohydrazono group and benzyl-CH₂ on carbon bearing COOH) | Benzenepropanoic acid, α-[(amino-iminomethyl)hydrazono]— |
| (structure with guanidinohydrazono group and CH₂CH₂CH₂CH₂CH₂CH₃ on carbon bearing COOH) | Octanoic acid, 2-[(aminoiminomethyl)-hydrazono]—, monohydrochloride |

TABLE 6

Dose-Response for Reduction in Hyperglycemia and Obesity in KKAy mice by Oral Administration of N-(dihydrazinomethylene)-glycine KKAy mice were treated with N-(dihydrazinomethylene)-glycine as described above except that the compound was admixed in the chow at 0.03, 0.06, 0.10, 0.20, 0.30, and 0.40% so as to deliver daily doses of approximately 30, 60, 100, 200, 300, and 400 mg/kg. Control mice received unsupplemented chow. For comparison to N-(dihydrazinomethylene)-glycine, 3-guanidinopropionic acid (3-GPA) was administered as a 0.50% admixture in the chow (approximate dose, 500 mg/kg/day). Data are shown as the percent change in blood glucose concentration and body weight on Day 3 compared to Day −1 of the study. Means ± S.E.M. for n = 6 mice/group. Statistical significance was determined by analysis of variance using JMP 3.0.2 software (SAS Institute). *, $P < 0.05$ vs. Nil; ¶, significantly less than 3-GPA ($P < 0.05$).

| Addition | % Change Blood Glucose | % Change Body Weight |
|---|---|---|
| Nil | −5.8 ± 7.1 | −0.71 ± 0.65 |
| 0.03% N-(dihydrazino methylene)-glycine | −13.5 ± 10.5 | −0.92 ± 0.35 |
| 0.06% N-(dihydrazino methylene)-glycine | −34.9 ± 17.1* | −1.51 ± 2.11 |
| 0.10% N-(dihydrazino methylene)-glycine | −45.2 ± 6.4* | −4.04 ± 0.76* |
| 0.2% N-(dihydrazino methylene)-glycine | −69.9 ± 3.2*,¶ | −8.22 ± 1.05* |
| 0.3% N-(dihydrazino methylene)-glycine | −70.4 ± 1.5*,¶ | −9.94 ± 1.62*,¶ |
| 0.4% N-(dihydrazino methylene)-glycine | −70.3 ± 3.9*,¶ | −10.3 ± 0.97*,¶ |
| 0.5% 3-GPA | −38.4 ± 0.4* | −5.4 ± 0.81* |

*, $P < 0.05$ vs. Nil
P, significantly less than 3-GPA ($P < 0.05$)

TABLE 7

Improvement of Intraperitoneal Glucose Tolerance

Glucose tolerance was measured in non-diabetic C57BL mice and diabetic KKAy mice. The animals were dosed by oral gavage with distilled water (Control) or 100 mg/kg of N-(dihydrazinomethylene)-glycine then fasted for 16–17 hours. Blood samples for glucose determination were obtained from the retro-orbital sinus. Samples were obtained immediately prior to administration of 2 g/kg glucose I.P. (Time = 0) and 30, 60, and 90 minutes after the injection. Blood glucose was determined using a glucose autoanalyzer. The data are expressed as means ± S.E.M. for 5–6 mice per group. Statistical significance was determined by analysis of variance using JMP 3.0.2 software (SAS Institute). *, $P < 0.05$ vs. Control.

| Mouse Strain | Group | Time (min.) | Blood Glucose (mg/dl) |
|---|---|---|---|
| C57BL | Control | 0 | 143 ± 8 |
| | | 30 | 233 ± 14 |
| | | 60 | 240 ± 8 |
| | | 90 | 226 ± 9 |
| | N-(dihydrazino-methylene)-glycine | 0 | 114 ± 9* |
| | | 30 | 174 ± 17* |
| | | 60 | 153 ± 7* |
| | | 90 | 161 ± 19* |
| KKAy | Control | 0 | 188 ± 43 |
| | | 30 | 487 ± 10 |
| | | 60 | 469 ± 20 |
| | | 90 | 486 ± 26 |
| | N-(dihydrazino-methylene)-glycine | 0 | 115 ± 16 (P = 0.12 vs. Control) |
| | | 30 | 383 ± 38* |
| | | 60 | 396 ± 63 |
| | | 90 | 392 ± 67 |

TABLE 8

Inhibition of Non-Enzymatic Glycosylation of Protein

Non-enzymatic glycosylation of protein was measured using established methods (Dolhofer and Wieland, 1979; Khatami, Suldan, David, Li, and Rockey, 1988). The incorporation of 100 mM [14C]-D-glucose into human serum albumin was determined by dissolving human serum albumin (Sigma Chemical Co.), [14C]-glucose, and glucose in a physiological saline solution and incubating at 37° C. for 8 days. Test compounds were added to the solution at 19.1 mM. Glycosylation of albumin was determined by precipitating the protein with 1 volume 12% trichloroacetic acid, centrifuging, and washing the pellet twice with 6% trichloroacetic acid with centrifugation following each wash. The washed pellet was solubilized, scintillant added and the incorporation of radiolabelled glucose determined by liquid scintillation counting. The data are expressed as the percent of [14C]-glucose incorporated into albumin (mean of 2 measurements). Statistical significance was determined by analysis of variance using JMP 3.0.2 software (SAS Institute).

| Substance Added | % [14C-glucose] Incorporated |
| --- | --- |
| Control (Nil) | 1.50 |
| Aminoguanidine | 0.96 (P < 0.05 vs. Control) |
| 3-Guanidinopropionic Acid | 1.52 |
| N-(dihydrazinomethylene)-glycine | 0.81 (P < 0.05 vs. Control) |
| N-(hydrazinoiminomethyl)-glycine monohydrochloride acetic acid | 1.21 (P < 0.05 vs. Control) 1.29 (P < 0. 10 vs. Control) |

TABLE 9

Intermediate Compounds

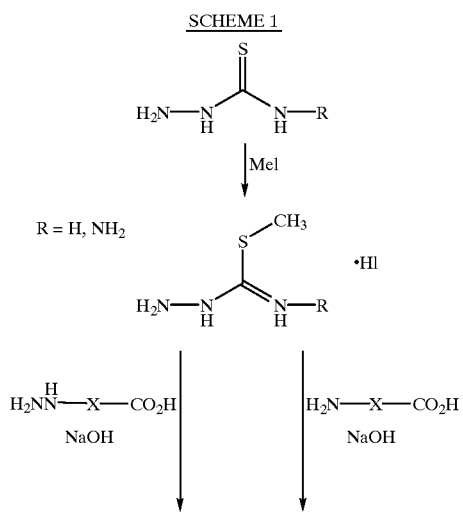

Compound A

Compound B

SCHEME 1

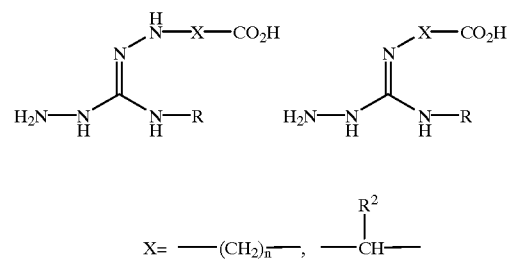

SCHEME 2

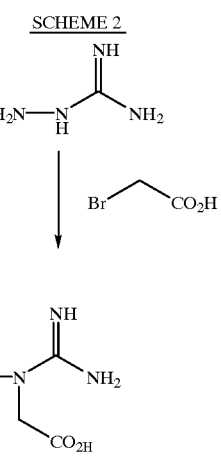

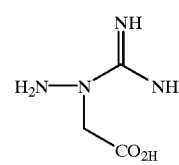

SCHEME 3

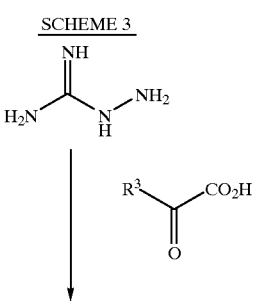

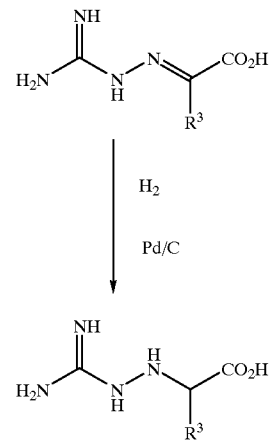

SCHEME 4
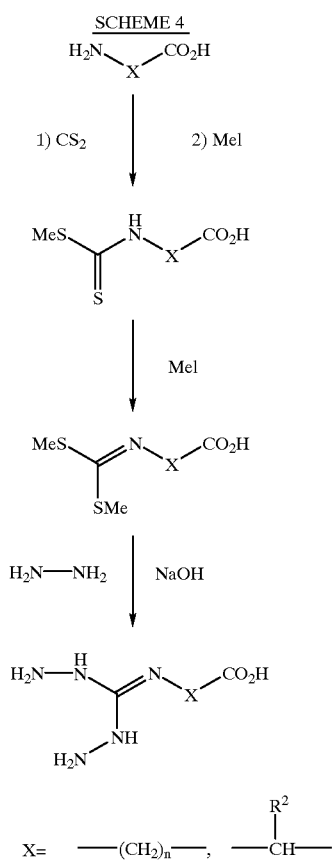
SCHEME 5
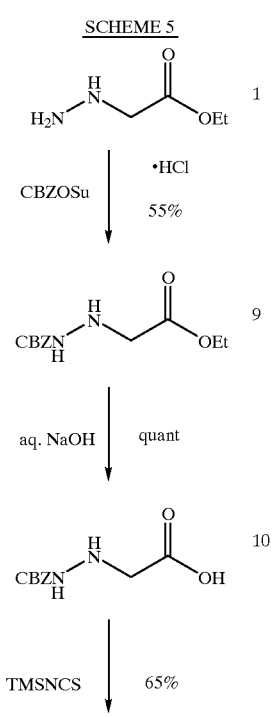
-continued
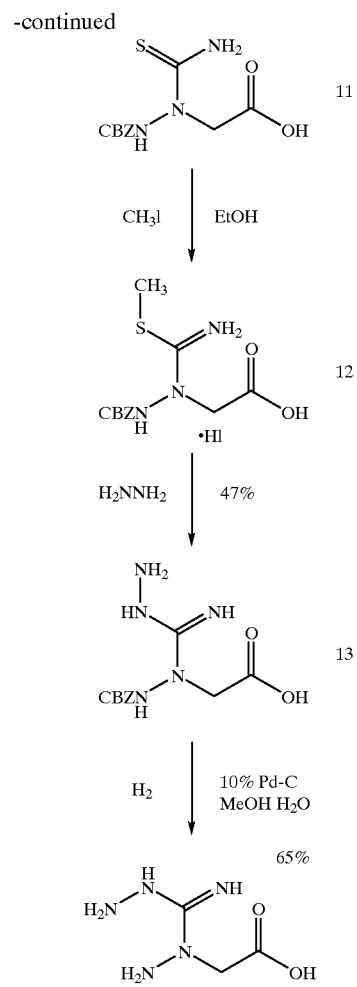
We claim:
1. A compound of the formula I or II:
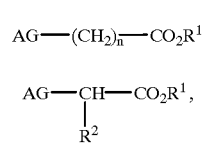
wherein AG is
  a) N-aminoguanidine,
  b) N,N'-diaminoguanidine, or
  c) N,N',N''-triaminoguanidine;
wherein n is an integer from 1–5
wherein $R^1$ is
  a) hydrogen
  b) phenyl
  c) $C_1$–$C_5$ alkyl, or
  d) $C_1$–$C_3$ alkyl-phenyl; and
wherein $R^2$ is
  a) phenyl,
  b) $C_1$–$C_{10}$ alkyl, or
  c) $C_1$–$C_5$ alkyl-phenyl,
a with the proviso that:

a) in formula I, when n is 2 or 3, $R^1$ is not hydrogen;
b) in formula I, when n is one, $R^1$ is not methyl;
c) in formula II, when $R^2$ is ethyl or phenyl, $R^1$ is not hydrogen
d) the compound of Formula I is not glycine, N-(hydrazinoiminomethyl)-; and
e) in formula II, when AG is aminoguanidine and $R^1$ is hydrogen, $R^2$ is not benzyl.

2. A compound selected from

[2-(aminoiminomethyl)hydrazino]acetic acid, its monohydride, and its phenylmethyl ester, monohydrochloride, α-[2-(aminoiminomethyl)hydrazino]benzenepropanoic acid monohydrate,

[1-(aminoiminomethyl)hydrazino]acetic acid monohydrobromide

N-(hydrazinoiminomethyl)-β-alanine,

N-(dihydrazinomethylene) glycine,

[2-(hydrazinoiminomethyl)hydrazine]acetic acid,

N-(dihydrazinomethylene)-β-alanine,

N-(dihydrazinomethylene)-L-alanine, racemic $HN=C(NH_2)-NH-NH-CH(CH_3)-COOH$,

N-(dihydrazinomethylene)-d-alanine, and

N-(dihydrazinomethylene)valine.

3. A compound selected from

[2-(aminoiminomethyl)hydrazino]acetic acid and its monohydrochloride,

N-(dihydrazinomethylene)glycine,

[2-(hydrazinoiminomethyl)hydrazino]acetic acid, and

[1-(hydrazinoiminomethyl)hydrazino]acetic acid.

* * * * *